United States Patent
Bischoff et al.

(10) Patent No.: US 11,241,336 B2
(45) Date of Patent: Feb. 8, 2022

(54) METHOD FOR EYE SURGERY (71) Applicant: Carl Zeiss Meditec AG, Jena (DE)

(72) Inventors: Mark Bischoff, Jena (DE); Manfred Dick, Gefell (DE)

(73) Assignee: CARL ZEISS MEDITEC AG, Jena (DE)

( * ) Notice: Subject to any disclaimer, the term of this patent is extended or adjusted under 35 U.S.C. 154(b) by 239 days.

(21) Appl. No.: 16/300,012

(22) PCT Filed: May 9, 2017

(86) PCT No.: PCT/EP2017/061102
§ 371 (c)(1),
(2) Date: Nov. 8, 2018

(87) PCT Pub. No.: WO2017/194567
PCT Pub. Date: Nov. 16, 2017

(65) Prior Publication Data
US 2019/0159934 A1 May 30, 2019

(30) Foreign Application Priority Data

May 10, 2016 (DE) .......................... 102016208012.1

(51) Int. Cl.
*A61F 9/008* (2006.01)
*A61F 9/013* (2006.01)
*A61F 9/009* (2006.01)
*A61F 2/16* (2006.01)

(52) U.S. Cl.
CPC ...... *A61F 9/00829* (2013.01); *A61F 9/00802* (2013.01); *A61F 9/00827* (2013.01);
(Continued)

(58) Field of Classification Search
CPC .............. A61F 9/00829; A61F 9/00802; A61F 9/00827; A61F 9/00831; A61F 9/00834;
(Continued)

(56) References Cited

U.S. PATENT DOCUMENTS

| 5,656,186 | A | 8/1997 | Mourou et al. |
| 8,486,055 | B2 | 7/2013 | Knox et al. |
| 9,241,901 | B2 | 1/2016 | Raymond et al. |
| 2004/0199149 | A1* | 10/2004 | Myers ................... A61F 9/008 606/4 |

(Continued)

FOREIGN PATENT DOCUMENTS

| DE | 41 31 361 A1 | 3/1993 |
| DE | 695 00 997 T2 | 4/1998 |

(Continued)

OTHER PUBLICATIONS

English Translation Cornea-Transplantation Bischoff, Mark; Stobrawa Gregor (Inventors). Zeiss Carl Meditec AG (Assignee). DE 102007019815 A1. (Published Oct. 30, 2008). (Year: 2008).*

*Primary Examiner* — Paula J Stice
(74) *Attorney, Agent, or Firm* — Christensen, Fonder, Dardi & Herbert PLLC (57) ABSTRACT

A planning system for generating control data for a treatment apparatus which creates at least one cut surface in the cornea using a laser device, and a treatment apparatus which comprises a planning system of the aforementioned type. The invention also relates to a method of generating control data for a treatment apparatus which creates at least one cut surface in the cornea using a laser device, and to a corresponding method of eye surgery. The planning system comprises a calculation means for defining the cut surfaces of the cornea, wherein the calculation means determines the cornea cuts so that the cut surfaces isolate a lenticule, which is treated according to the planned refraction correction after removal from the cornea, so that the planned refraction correction occurs after the insertion into the cornea of the recipient.

20 Claims, 4 Drawing Sheets (52) U.S. Cl.
CPC ...... *A61F 9/00831* (2013.01); *A61F 9/00834* (2013.01); *A61F 9/013* (2013.01); *A61F 2/16* (2013.01); *A61F 9/009* (2013.01); *A61F 2009/0088* (2013.01); *A61F 2009/00872* (2013.01)

(58) Field of Classification Search
CPC .. A61F 9/013; A61F 9/009; A61F 2/16; A61F 2009/00872; A61F 2009/0088
See application file for complete search history.

(56) References Cited

U.S. PATENT DOCUMENTS

| | | |
|---|---|---|
| 2008/0114283 A1 | 5/2008 | Mattson et al. |
| 2008/0183159 A1 | 7/2008 | Preuss et al. |
| 2008/0275433 A1 | 11/2008 | Russmann et al. |
| 2010/0087802 A1 | 4/2010 | Bischoff et al. |
| 2012/0059439 A1 | 3/2012 | Yoon |
| 2014/0081249 A1 | 3/2014 | Bischoff et al. |
| 2014/0264980 A1 | 9/2014 | Muller |

FOREIGN PATENT DOCUMENTS

| | | |
|---|---|---|
| DE | 199 43 723 A1 | 4/2001 |
| DE | 199 43 735 A1 | 5/2001 |
| DE | 10 2005 040 338 A1 | 3/2007 |
| DE | 10 2007 019 813 A1 | 10/2008 |
| DE | 10 2007 019 815 A1 | 10/2008 |
| DE | 10 2013 218 415 A1 | 4/2014 |
| WO | WO 2009/158723 A2 | 12/2009 |
| WO | WO 2012/035403 A1 | 3/2012 |

\* cited by examiner

METHOD FOR EYE SURGERY

PRIORITY CLAIM

The present application is a National Phase entry of PCT Application No. PCT/EP2017/061102, filed May 9, 2017, which claims priority from German Application Number 10 2016 208 012.1 filed May 10, 2016, the disclosures of which are hereby incorporated by reference herein in their entirety.

FIELD OF THE INVENTION

The invention relates to a planning device for producing control data for a treatment apparatus, which produces at least one cut surface in the cornea by means of a laser device. The invention further relates to a treatment apparatus comprising a planning device of the aforementioned type.

The invention further relates to a method for producing control data for a treatment apparatus, which produces at least one cut surface in the cornea by means of a laser device.

Finally, the invention likewise relates to a method for eye surgery, wherein at least one cut surface in the cornea is produced by means of a treatment apparatus with a laser device.

BACKGROUND OF THE INVENTION

The prior art has disclosed very different treatment methods that have the correction of refraction at the human eye as a target. Here, the object of the surgical methods is to modify the cornea in a targeted manner in order thus to influence the light refraction in the eye. A plurality of surgical methods are used to this end. The most widespread method is the so-called laser in situ keratomileusis, which is also abbreviated LASIK. Here, a corneal lamella is detached from the corneal surface on one side and folded to the side. This lamella can be detached by means of a mechanical microkeratome, or else by means of a so-called femtosecond laser keratome, as distributed by Intralase Corp., Irvine, USA, for example. After the lamella has been detached and folded to one side, the application of an excimer laser is provided in the LASIK surgery, said excimer laser removing the corneal tissue exposed in this way from under the lamella by ablation. After the corneal tissue, which originally lay under the corneal surface, has been evaporated from the surface in this way, the corneal lamella is folded back onto its original place again.

The application of a laser keratome for exposing the lamella is advantageous over a mechanical knife since the geometric precision is improved and the frequency of clinically relevant complications is reduced. In particular, the lamella can be produced with a very much more constant thickness if laser radiation is used. Additionally, the cut edge is formed precisely, which reduces the risk of an impairment to healing as a result of this boundary that also still remains after the operation. However, a disadvantage of this method is that two different treatment apparatuses have to be used, namely, firstly, the laser keratome for exposing the lamella and, secondly, the laser that evaporates the corneal tissue.

These disadvantages have been remedied in a method which was recently implemented by Carl Zeiss Meditec AG and which is abbreviated by FLEX (femtosecond lenticule extraction). In this method for lenticule extraction, a cut geometry which separates a corneal volume (a so-called lenticule) in the cornea is formed in the cornea of the eye by means of a short-pulse laser, preferably a femtosecond laser. Said lenticule is then manually removed by the surgeon after the lamella covering the lenticule has been folded to the side. The advantage of this method lies in the fact that, firstly, the cut quality is once again improved by applying the femtosecond laser in combination with a curved contact glass. Secondly, only one treatment apparatus is required; the excimer laser is no longer used. This method also avoids the risks and limitations of the excimer laser.

These days, a development of the FLEx method is referred to in the literature as the SMILE method; here, it is no longer a flap that is produced but only small opening incision as an access to the lenticule that lies under the so-called cap. The separated lenticule is removed through this small opening incision, as a result of which the biomechanical integrity of the front cornea is impaired less than in the case of LASIK or similar methods. Additionally, fewer nerve fibers in the cornea are severed near the surface in this way, which probably has an advantageous effect on the re-establishment of the original sensitivity of the corneal surface. The symptom of dry eyes, which often has to be treated after LASIK, is thereby reduced in terms of its manifestation and duration. Other complications after LASIK, too, which are usually in connection with the flap (e.g., flap displacement, folds, epithelial growth in the flap bed), occur less frequently without a flap.

When producing cut surfaces in the cornea by means of laser radiation, the optical radiation effect is usually exploited by virtue of an optical breakdown being produced by individual optical pulses, the duration of which may lie between approximately 100 fs and 100 ns. In addition, the practice of introducing individual pulses, whose energy lies below a threshold for an optical breakdown, into the tissue or material with such overlay that this also achieves a material or tissue separation is known. This concept of producing cuts in the corneal tissue allows a large variety of cuts.

What is common to all of these known methods is that the treatment success depends on the reliable immobilization of the eye to be treated since even small movements lead to a deviation from the envisaged refraction correction and hence lead to an induced refractive error.

SUMMARY OF THE INVENTION

The invention is therefore based on the object of specifying a planning device for producing control data, a treatment apparatus for refraction-correcting eye surgery and a method for producing control data for such a treatment apparatus, in which method an improved refraction correction is ensured.

According to the invention, this object is achieved by a planning device of the type set forth at the outset, said planning device having calculation means for setting, determining or defining corneal cut surfaces, wherein the calculation means, which may include a computer, determine the cut surfaces in such a way that a lenticule is isolated by the cut surfaces, said lenticule being treated according to the planned refraction correction after removal from the donor cornea such that, after insertion into the recipient cornea, the planned refraction correction results or sets in.

In comparison with other tissue types or organs, corneal tissue can easily be transplanted from a donor to a recipient. The probability of complications is even lower if this is an autogenous transplant, which is why this variant of the method is likewise important for the application. Thus, in a special form of the method, donor and recipient are identical.

In a further variant of the method, the donor cornea consists of tissue or material produced by technological means, which is used instead of conventional donor material. In order to promote a problem-free implantation into the recipient cornea, an appropriately formed lenticule is removed from the latter and replaced by the implant. The tissue or material produced by technological means can also be produced by a technological process using human donor tissue, for example.

Further, the invention is achieved by a treatment apparatus having a laser device, which separates at least one cut surface in the cornea by means of laser radiation in accordance with control data, and a planning device of the type just specified above for producing the control data, wherein the planning device determines the cut surfaces in such a way that a lenticule is isolated by the cut surfaces, said lenticule being treated according to the planned refraction correction after removal from the donor cornea such that, after insertion into the recipient cornea, the planned refraction correction results.

Finally, the invention is likewise achieved by a method for producing control data according to the type set forth at the outset, said method including: producing a control data record for the corneal cut surface for actuating the laser device, wherein the planning device determines the cut surfaces in such a way that a lenticule is isolated by the cut surfaces, said lenticule being treated according to the planned refraction correction after removal from the donor cornea such that, after insertion into the recipient cornea, the planned refraction correction results.

Finally, the invention is likewise achieved by a method, including: producing a control data record for the corneal cut surface, transmitting the control data to the treatment apparatus and producing the cut surfaces by actuating the laser device with the control data record, wherein, when producing the control data record, the cut surfaces are determined in such a way that a lenticule is isolated by the cut surfaces, said lenticule being treated according to the planned refraction correction after removal from the donor cornea such that, after insertion into the recipient cornea, the planned refraction correction results.

Consequently, the invention relates to an apparatus and a method which improve refractive surgery by virtue of tissue removed from the eye being treated outside of the eye and subsequently being reimplanted in the original eye or a different eye.

The tissue is preferably the cornea or the lens of the eye.

The treatment brings about a change in physical, chemical or biological properties, in particular a change in optical properties.

The treatment is implemented by the interaction of the explanted tissue with substances and/or with radiation, for example with radiation from lasers.

As substances, use is made of, e.g., photosensitizers (e.g., riboflavin), IOP-reducing (IOP=intraocular pressure) pharmaceuticals, antimycotics, antibiotics, stem cells or nanoparticles.

UV light sources and/or ultra-short pulse lasers are preferably used as radiation sources for the external treatment.

The change in the properties relates, in particular, to the form and/or refractive index of the removed material/tissue.

The invention employs the prior art in relation to the extraction of a lenticule with a defined refractive power for the purposes of extracting a lenticule, which is referred to below as a design lenticule in order to provide a better distinction from the "conventional" lenticule for correcting the refractive power.

In order to obtain a high level of safety for the patient, the form of the design lenticule is advantageously selected in such a way that the removal thereof does not lead to an unacceptable refractive result of the treatment for the donor or receiver. This procedure is particularly advantageous for the autogenous method variant. Thus, it may be indicated for medical reasons that the design lenticule be removed again by surgery some time after the transplant, be it due to a side effect or because it should be subjected to a new external treatment. By way of example, the form of the design lenticule can be adapted for the refractive correction of a manifest refractive error of the eye by means of lenticule extraction (SMILE).

Therefore, design lenticules with such a geometry that precisely obtain no refractive effect are of particular interest. These have an approximately constant thickness but have an adapted profile curve which does not substantially change the refractive power of the cornea upon their removal.

The following, inter alia, are available as treatment methods for the refraction correction that is to be undertaken externally:

cross-linking the lenticule in order to thicken and/or change the refractive index for the purposes of a refractive correction (e.g., US 2008/0114283, US 2012/059439, the content of which is incorporated herein by reference). In the process, the design lenticule is removed, e.g., treated with riboflavin or another suitable substance, irradiated by UV light in a targeted manner and subsequently reinserted into the cornea of the patient, treating the lenticule with nanoparticles for the purposes of a targeted change in the refractive power as described in U.S. Pat. No. 9,241,901, the content of which is incorporated herein by reference; after the treatment, the design lenticule is reinserted into the cornea of the patient, treating the lenticule with laser radiation such that there is a local change the refractive power (LIRIC=Laser-induced Refraction Index Change, DE 41 31 361, DE 199 43 723 and DE 199 43 735 by the applicant, U.S. Pat. No. 8,486,055 Knox et al., the content of which is incorporated herein). This effect can also be used to produce refractive and/or diffractive structures that modify the imaging properties of the entire eye in such a way that an existing refractive error can be compensated. In analogous fashion, it is also possible to write gradient index profiles (GRIN), wherein the effectiveness of the writing process still can be increased significantly by the addition of photosensitizers (e.g., sodium fluorescein). According to the invention, a design lenticule is removed, treated by the ultra-short pulse laser and reimplanted.

Treating the lenticule by means of ablating UV radiation in order to produce a geometry that is adapted to the desired refractive change, and subsequently reinserting the design lenticule thus treated.

Treating the lenticule by means of a cutting fs-laser like in the cut creation prior to removal in order to produce an adapted geometry and thus a geometry that is adapted to the desired refractive change, and subsequently reinserting the design lenticule thus treated.

Treating the lenticule for conservation purposes, e.g. for storage in liquid nitrogen and for preparing for implantation after the end of the storage.

The apparatus according to the invention for the external treatment of lenticules comprises, inter alia, the following features:

A holding apparatus for lenticules, which facilitates mounting of the lenticules in the correct form, for example, by way of a preferably spherically curved surface that approximately has the radius of curvature of a lenticule.

Optional: a fixation apparatus for lenticules, which facilitates a fold-free fixation of lenticules, for example a preferably spherically curved element which, together with the holding apparatus, encloses the lenticule.

The fixation apparatus or holding apparatus are transparent to the treatment radiation, A radiation source (laser, LED, lamp), A beam-shaping device for shaping and/or deflecting a beam, A controller for controlling the radiation source, beam shaping, beam deflection, Optional: a focusing apparatus, Optional: means for controlled exposure of the lenticule to photosensitizers (e.g. riboflavin), IOP-reducing pharmaceuticals, antimycotics, antibiotics, stem cells or nanoparticles, Means for calculating an irradiation pattern, wherein the irradiation pattern being representable as an intensity profile of the radiation in respect of the coordinate system of the lenticule (x, y, z), Optional: means for calculating an exposure pattern, wherein the exposure pattern is representable as a concentration profile of the substance in relation to the lenticule, Means for determining a coordinate transformation from appliance coordinates to lenticules coordinates, for example by measuring object points in both coordinate systems or by measuring reference points in the holding apparatus or fixation apparatus, Optional: means for producing a holographic illumination of the lenticule with treatment radiation, Optional: means for producing an interferometric illumination of the lenticule with treatment radiation.

Here, this treatment apparatus can either be constructed separately from the treatment apparatus that is provided for removing the lenticule, or else it can be integrated in said treatment apparatus, as a result of which some components (e.g., laser, scanner, controller) can be used together. To this end, the laser can have a switchable embodiment in respect of wavelength and/or pulse energy. During the treatment of the design lenticule, the patient can be moved out of the treatment apparatus and a holder for the design lenticule can be introduced in their place; alternatively, the treatment radiation for the design lenticule can also be coupled out of the treatment apparatus by way of a beam splitter.

It is understood that the features mentioned above and features yet to be explained below can be used not only in the specified combinations but also in other combinations or on their own, without departing from the scope of the present invention.

BRIEF DESCRIPTION OF THE DRAWINGS

Below, the invention will still be explained in more detail in exemplary fashion on the basis of the attached drawings, which also disclose features that are essential to the invention. In detail.

DETAILED DESCRIPTION

Figure 1:
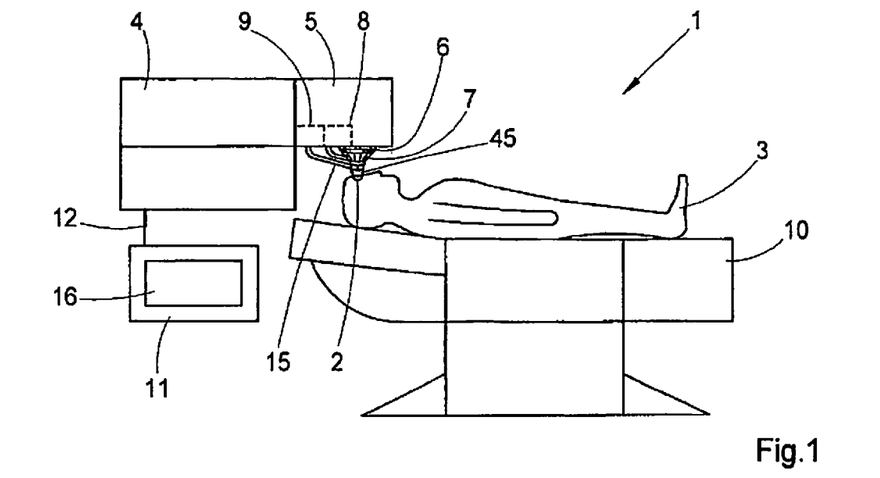
FIG. 1 shows a schematic illustration of a treatment apparatus with a planning device for a treatment in the case of eye-surgical refraction correction.

A treatment apparatus for eye surgery is illustrated in FIG. 1 and denoted by the general reference sign 1. The treatment apparatus 1 is embodied to introduce laser cuts on an eye 2 of a patient 3. To this end, the treatment apparatus 1 comprises a laser device 4, which emits a laser beam 6 from a laser source 5, said laser beam being directed into the eye 2 or the cornea of the eye as a focused beam 7. Preferably, the laser beam 6 is a pulsed laser beam with a wavelength of between 300 nanometers and 10 micrometers. Further, the pulse length of the laser beam 6 lies in the range between 1 femtosecond and 100 nanoseconds, wherein pulse repetition rates of 500 to 50 000 kilohertz and pulse energies between 0.01 microjoule and 0.01 millijoule are possible. Consequently, the treatment apparatus 1 produces a cut surface in the cornea of the eye 2 by way of deflection of the pulsed laser radiation. Therefore, a scanner 8 and a radiation intensity modulator 9 are also provided to this end in the laser device 4 or the laser source 5 thereof.

The patient 3 is situated on a couch 10, which is optionally adjustable in three spatial directions in order to align the eye 2 in a manner fitting to the incidence of the laser beam 6. The couch 10 is adjustable by motor in a preferred construction. As an alternative, the patient couch is less movable and, instead, the treatment apparatus is correspondingly adjustable by motor. In particular, actuation can be brought about by a controller 11 which, in principle, controls the operation of the treatment apparatus 1 and, to this end, is connected to the treatment apparatus by way of suitable data connections, connection lines 12, for example. Naturally, this communication can also be implemented in a different fashion, for example, by way of light guides or by radio. The controller 11 undertakes the corresponding settings and time control at the treatment apparatus 1, in particular the laser device 4 and consequently brings about corresponding functions of the treatment apparatus 1.

The treatment apparatus 1 further comprises an immobilization device 15, which immobilizes the position of the cornea of the eye 2 in relation to the laser device 4. This immobilization device 15 may comprise a contact glass 45, known per se, to which the cornea of the eye is applied by negative pressure and which impresses a desired geometric form on the cornea of the eye. Such contact glasses are known to a person skilled in the art from the prior art, for example from DE 102005040338 A1. To the extent that this relates to the description of the structure of the contact glass 45 that is available to the treatment apparatus 1, the disclosure of this document is incorporated herein in the entirety thereof. Other modified or improved contact glass forms could also be advantageous for the invention and should therefore be included.

The treatment device 1 furthermore comprises a camera (not illustrated here), which is able to record an image of the cornea 17 of the eye through the contact glass 45. Here, the illumination for the camera can be implemented both in the visible and in the infrared range of light.

The controller 11 of the treatment apparatus 1 further comprises a planning device 16, which will still be explained in more detail below.

Figure 2:
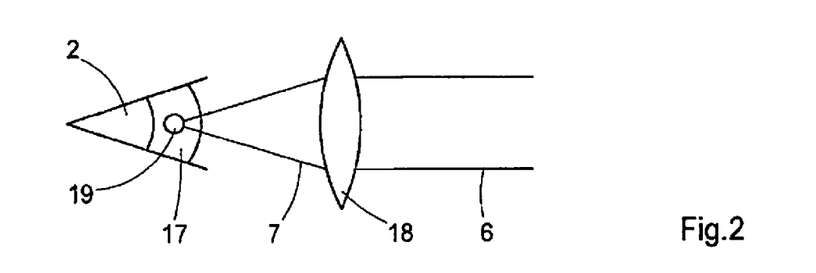
FIG. 2 shows a schematic illustration of the effect of the laser radiation that is used in the treatment apparatus of FIG. 1.

FIG. 2 schematically shows how the incident laser beam 6 acts. The laser beam 6 is focused and incident as the focused laser beam 7 in the cornea 17 of the eye 2. A schematically plotted optical unit 18 is provided for focusing purposes. It brings about a focus in the cornea 17, the laser radiation energy density being so high in said focus that, in combination with the pulse length of the pulsed laser radiation 6, a further nonlinear effect occurs in the cornea 17. By way of example, each pulse of the pulsed laser radiation 6 can produce an optical breakdown in the cornea 17 of the eye in the focus 19, said optical breakdown in turn initiating a plasma bubble that is only schematically indicated in FIG. 2. When the plasma bubble arises, the tissue layer separation comprises a larger area than the focus 19 even though the conditions for producing the optical breakdown are only achieved in the focus 19. So that an optical breakdown is produced by each laser pulse, the energy density, i.e., the fluence of the laser radiation, must lie above a certain, pulse-length-dependent threshold. A person skilled in the art knows of this relationship, for example from DE 69500997 T2. Alternatively, a tissue-separating effect can also be achieved by pulsed laser radiation by virtue of a plurality of laser radiation pulses being emitted in a region, with the focal spots overlapping. Then, a plurality of laser radiation pulses work together to obtain a tissue-separating effect. The type of tissue separation used by the treatment apparatus 1 is, however, of no further relevance to the description below; all that is essential is that a cut surface is generated in the cornea 17 of the eye 2.

The invention improves the pressure equalization in the region of the plasma bubbles while the latter are produced and thus improves the cut quality by reducing the tissue disturbance during the cutting process.

In order to carry out an eye-surgical refraction correction, a corneal volume is removed by means of laser radiation 6 from a region within the cornea 17 by virtue of tissue layers being separated therein, said tissue layers isolating the corneal volume and then facilitating the removal thereof. For the purposes of isolating the corneal volume to be removed, the position of the focus 19 of the focused laser radiation 7 in the cornea 17 is adjusted in the case of laser radiation that is introduced in pulsed fashion, for example. This is shown schematically in FIG. 3. The refractive properties of the cornea 17 are modified in a targeted manner by the removal of the volume in order thus to achieve the refraction correction. The volume is therefore usually lens-shaped and referred to as a lenticule.

Figure 3:
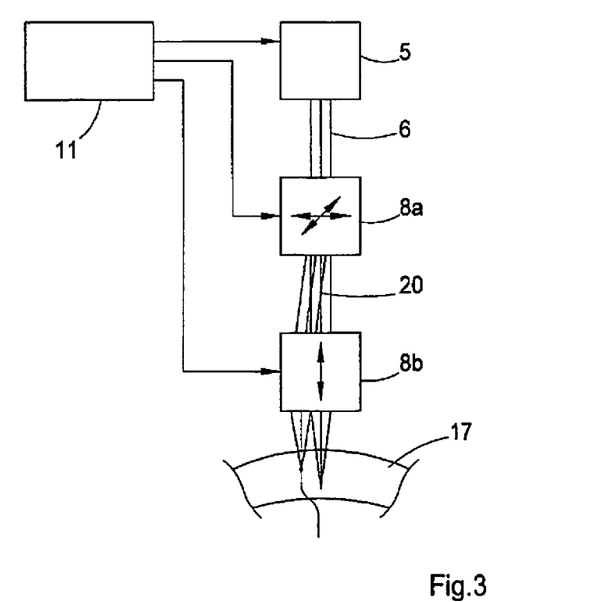
FIG. 3 shows a further schematic illustration of the treatment apparatus of FIG. 1 in respect of the introduction of the laser radiation.

In FIG. 3, the elements of the treatment apparatus 1 are only plotted to the extent that they are required for the understanding of the cut surface production. As already mentioned, the laser beam 6 is focused in a focus 19 in the cornea 19 and the position of the focus 17 in the cornea is adjusted such that, for the cut surface production, focused energy from laser radiation pulses is introduced into the tissue of the cornea 17 at different locations. The laser radiation 6 is preferably provided as pulsed radiation by the laser source 5. In the structure of FIG. 3, the scanner 8 is of two-part design and consists of an xy-scanner 8a, which is realized by two galvanometer mirrors that substantially deflect in orthogonal fashion in one variant. The scanner 8a deflects the laser beam 6 coming from the laser source 5 in two-dimensional fashion such that a deflected laser beam 20 is present after the scanner 8. Consequently, the scanner 8a brings about an adjustment in the position of the focus 19, substantially perpendicular to the principal direction of incidence of the laser beam 6 in the cornea 17. In addition to the xy-scanner 8a, a z-scanner 8b is also provided in the scanner 8 for the purposes of adjusting the depth position, said z-scanner being embodied as an adjustable telescope, for example. The z-scanner 8b ensures a change in the z-position of the position of the focus 19, i.e., the position thereof along the optical axis of incidence. The z-scanner 8b can be disposed upstream or downstream of the xy-scanner 8a.

The assignment of the individual coordinates to the spatial directions is not essential to the functional principle of the treatment apparatus 1, and nor is it that the scanner 8a deflects about axes that are orthogonal to one another. Instead, use can be made of any scanner that is able to adjust the focus 19 in a plane not including the axis of incidence of the optical radiation. Further, it is also possible to use arbitrary non-Cartesian coordinate systems for deflecting or controlling the position of the focus 19. Examples to this end include spherical coordinates and cylindrical coordinates. The position of the focus 19 is controlled by means of the scanners 8a, 8b under actuation by the controller 11, which undertakes appropriate settings at the laser source 5, the modulator 9 (not shown in FIG. 3) and the scanner 8. The controller 11 ensures a suitable operation of the laser source 5 and the three-dimensional focus adjustment explained herein in exemplary fashion such that, ultimately, a cut surface is formed, said cut surface isolating a certain corneal volume that should be removed for the purposes of correcting the refraction.

The control device 11 operates according to predetermined control data that, for example, are predetermined as target points for the focus adjustment in the laser device 4 that is only explained in exemplary fashion here. As a rule, the control data are combined in a control data record. The latter yields geometric prescriptions for the cut surface to be formed, for example the coordinates of the target points as a pattern. Then, in this embodiment, the control data record also contains specific values for the focal position adjustment mechanism, e.g., for the scanner 8.

Figure 4:
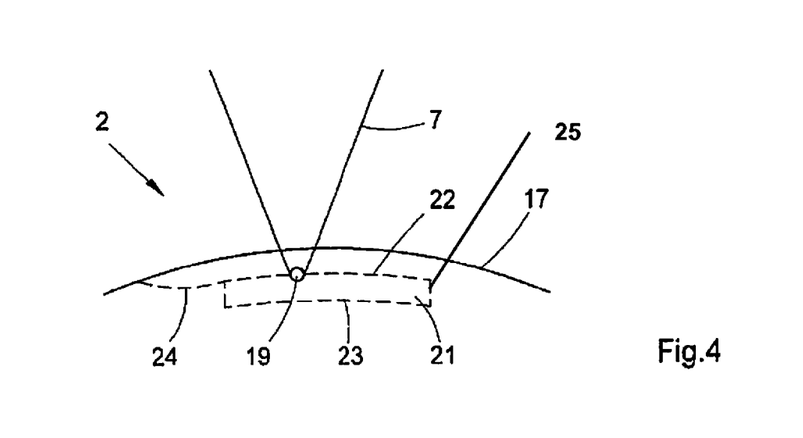
FIG. 4 shows a schematic sectional illustration through the cornea of an eye for elucidating the removal of the corneal volume in conjunction with the eye-surgical refraction correction.

Producing the cut surface with the treatment apparatus 1 is shown in FIG. 4 in exemplary fashion. A corneal volume 21 in the cornea 17 is isolated by adjusting the focus 19, in which the focused beam 7 is focused. To this end, cut surfaces are formed, said cut surfaces being formed here as an anterior flap cut surface 22 and as a posterior lenticule cut surface 23 in an exemplary fashion. These terms should only be understood in exemplary fashion here and should establish the relationship to the conventional Lasik or Flex method, for which the treatment apparatus 1, as already mentioned above, is likewise embodied. All that is essential here is that the cut surfaces 22 and 23 and the circumferential side cut 25, which brings together the cut surfaces 22 and 23 at the edges thereof, isolate the corneal volume 21. By way of an opening incision 24, it is further possible to fold away a corneal lamella that delimits the corneal volume 21 in the anterior direction such that the corneal volume 21 is removable.

In an alternative, and for the present invention essential manner, the SMILE method can be used; here, the corneal volume 21 is removed through a small opening incision, as described in DE 10 2007 019813 A1. The disclosure of this document is incorporated herein by reference in its entirety.

Figure 5:
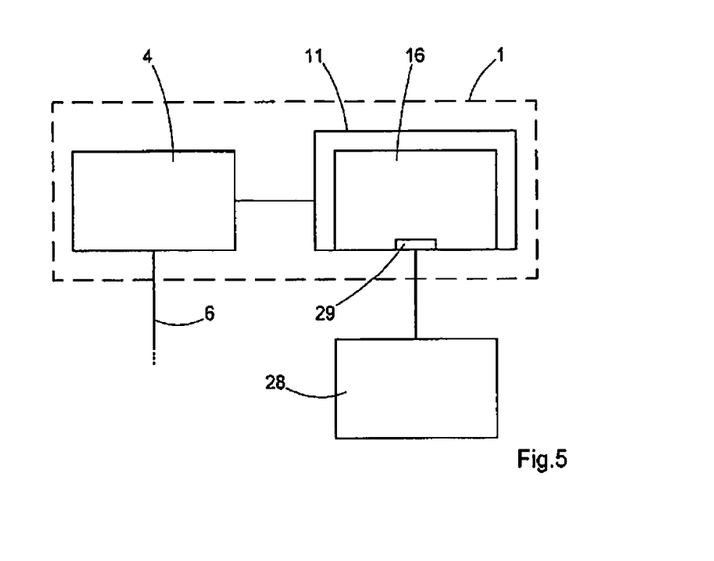
FIG. 5 shows a schematic illustration in respect of the construction of the treatment apparatus of FIG. 1, with particular reference to the planning device present there.

FIG. 5 schematically shows the treatment apparatus 1 and it should be used to explain the importance of the planning device 16 in more detail. In this variant, the treatment apparatus 1 comprises at least two devices or modules. The already explained laser device 4 outputs the laser beam 6 onto the eye 2. Here, as already explained, the operation of the laser device 4 is fully automatic by way of the controller 11, i.e., the laser device 4 starts the production and deflection of the laser beam 6 following an appropriate activation signal and produces cut surfaces in the process, said cut surfaces being constructed as described above. The control signals required for the operation are received by the laser device 5 from the controller 11, the latter being provided with appropriate control data in advance. This is implemented by means of the planning device 16, which is shown in a purely exemplary manner as a constituent part of the controller 11 in FIG. 5. Naturally, the planning device 16 can also have an independent embodiment and can communicate with the control device 11 in a wired or wireless fashion. All that is essential in that case is that a corresponding data transmission channel is provided between the planning device 16 and the controller 11.

The planning device 16 produces a control data record which is made available to the controller 11 for the purposes of carrying out the eye-surgical refraction correction. Here, the planning device uses measurement data about the cornea of the eye. In the embodiment described here, these data originate from a measuring device 28, which had previously measured the eye 2 of the patient 3. Naturally, the measuring device 28 can be embodied in any way and transfer the appropriate data to the interface 29 of the planning device 16.

The planning device now assists the operator of the treatment apparatus 1 when setting the interface for isolating the corneal volume 21. This can go as far as fully automatically setting the cut surfaces, which may be brought about by virtue of, for example, the planning device 16 establishing the corneal volume 21 to be removed from the measurement data, defining the delimiting surfaces thereof as cut surfaces and producing appropriate control data for the controller 11 therefrom. At the other end of the degree of automation, the planning device 16 can provide input options at which a user enters the cut surfaces in the form of geometric parameters, etc. Intermediate stages provide suggestions for the cut surfaces, which are automatically generated by the planning device 16 and which are then modifiable by a user. In principle, all concepts that were already explained above in the more general part of the description can be used here in the planning device 16.

In order to carry out a treatment, the planning device 16 produces control data for the cut surface production, which then are used in the treatment apparatus 1.

Figure 6:
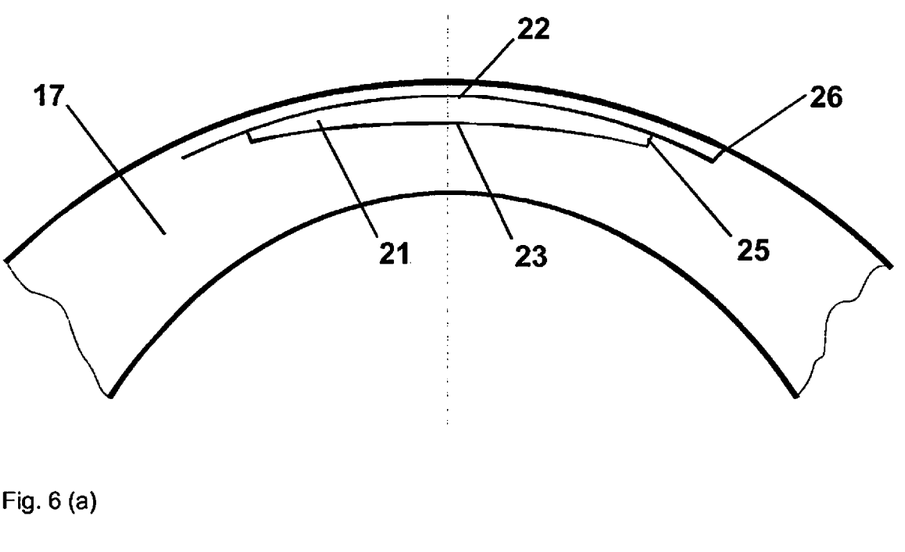
FIG. 6 shows a schematic illustration of a lenticule geometry.

FIG. 6a shows a schematic illustration of a corneal cross section in the SMILE method for clarification of the geometric relationships of the lenticule to be removed. The cornea 17 has as an anterior cap cut 22 with an opening incision 26. The posterior lenticule cut 23 isolated the lenticule volume 21, which can be removed through the opening incision 26.

FIG. 6b shows a plan view of the cornea illustrated in FIG. 6a with the lenticule 21. Here, the lenticule is formed in such a way that the removal thereof does not cause a change in the refraction conditions in the eye, and hence the entire refraction correction is undertaken externally on the removed lenticule. This is advantageous in that there is no deterioration in the visual acuity even in the case of complications (errors in the external refraction correction, rejection, or the like, of the lenticule after reinsertion).

Figure 7:
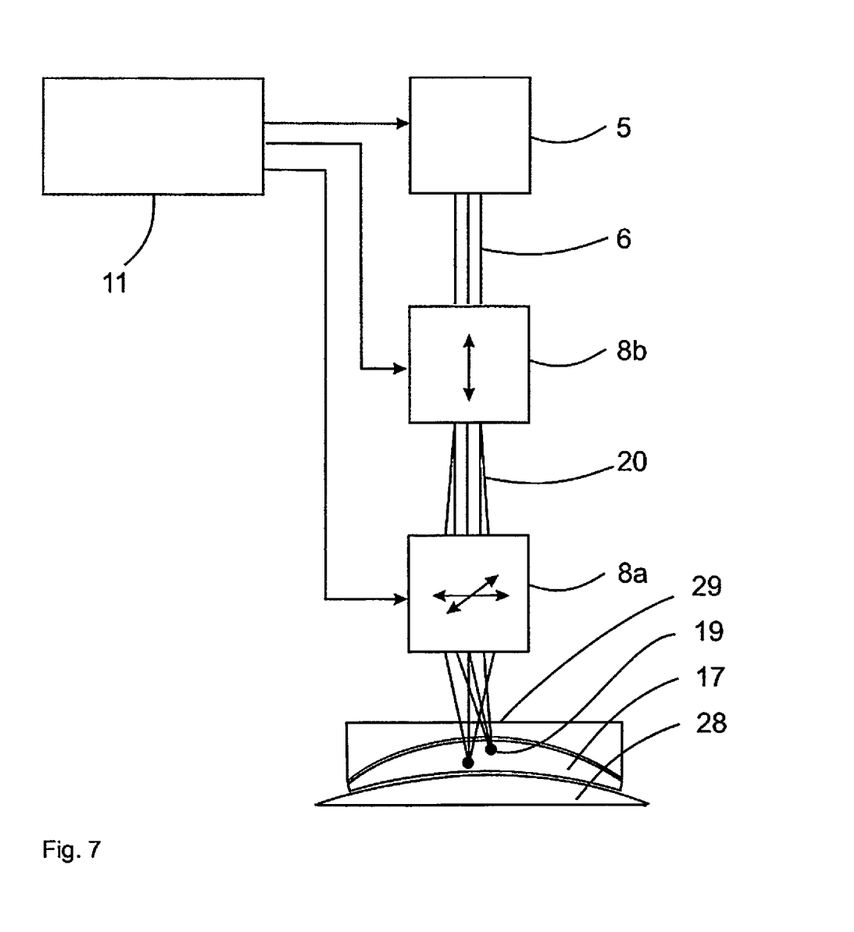
FIG. 7 shows a schematic illustration of an external treatment apparatus for the design lenticule.

In the style of FIG. 5, FIG. 7 shows a schematic illustration of an external treatment apparatus for the design lenticule. Beyond the constituent parts that are already present in FIG. 5 and that are explained further above, said external treatment apparatus comprises a holding apparatus for the design lenticule 17, which consists of a support structure 28 and a contact glass 29. The design lenticule is held between the support structure 28 and the contact glass 29, with it being brought into a defined form by the radii of the contact surfaces, said form being taken into account when calculating the treatment pattern (by way of appropriate coordinate transforms). In the exemplary embodiment explained here, the available fs-laser lends itself to undertaking the treating of the design lenticule and hence cutting lends itself to obtaining the desired form. Alternatively, one of the treatment methods explained further above (cross-linking, nanoparticles, laser-induced refractive index change (LIRIC) or ablation) can naturally also be used.

Then, the steps of the method for refraction correction are:
  determining the correction requirement (pachymetry, aberrometry, wavefront analysis),
  isolating and removing the design lenticule from the patient's eye,
  positioning the design lenticule in the holding apparatus,
  determining the control data for treating the design lenticule depending on the selected treatment method,
  reinserting the design lenticule into the patient's eye.

Should a non-symmetric correction requirement (astigmatism) arise, reference marks can additionally be introduced into the cornea and/or the design lenticule for reestablishing the spatial relationship.

Additionally, it should be noted that the treatment apparatus 1 or the planning device 16 naturally also specifically realizes the implementation of the method explained in general terms above.

A further embodiment of the planning device consists in the form of a computer program or a corresponding data medium with a computer program, which realizes the planning device on a corresponding computer such that the input of the measurement data is implemented by way of suitable data transmission means to the computer and the control data are transferred from this computer to the controller 11, for the purposes of which, once again, data transmission means known to a person skilled in the art come into question.

While the invention is illustrated in detail in the drawings and the description above, the illustration and description should be considered as explanatory or exemplary and as non-restrictive. It is understood that changes and modifications within the scope of the following claims can be undertaken by a person skilled in the art. In particular, the present invention comprises further embodiments with any combination of features of different embodiments described above and below.

The invention claimed is:

1. A planning device for producing control data for a treatment apparatus for eye surgery, which produces at least one cut surface in a donor cornea by means of a laser device, the planning device comprising:

a computer configured to determine corneal cut surfaces and to produce a control data record for actuating the laser device, wherein the computer determines the corneal cut surfaces in such a way that a lenticule is isolated in the donor cornea by the corneal cut surfaces;

said lenticule after removal from the donor cornea being treated to change an optical property of the lenticule according to a planned refraction correction such that, after insertion of the treated lenticule into a recipient cornea, the planned refraction correction results.

2. The planning device as claimed in claim 1, wherein a human donor of the donor cornea and a human recipient of the donor cornea are the same human.

3. The planning device as claimed in claim 1, wherein the removal of the lenticule from the donor cornea does not change a refraction of the donor eye.

4. The planning device of claim 1, wherein the corneal cut surfaces include at least one of a cap cut and a lenticular cut.

5. The planning device of claim 1, wherein said treatment comprises changing a physical, chemical or biological property of the lenticule.

6. The planning device of claim 5, wherein said treatment comprises changing a physical property of the lenticule resulting in a change to an optical power of the lenticule.

7. A treatment apparatus for eye surgery, comprising:
a laser device which produces at least one cut surface in a cornea using laser radiation in accordance with control data, and
the planning device for producing the control data as claimed in claim 1.

8. The treatment apparatus as claimed in claim 7, wherein the removal of the lenticule from the donor cornea, does not change a refraction of the donor eye.

9. A method for producing control data for a treatment apparatus for eye surgery, which produces at least one cut surface in a donor cornea using a laser device, the method comprising the following steps:
providing corneal data that is based on data of a refraction correction,
setting the corneal cut surfaces, and
producing a control data record for the corneal cut surfaces for actuating the laser device,
wherein the corneal cut surfaces are determined in such a way that a lenticule in the donor cornea is isolated by the corneal cut surfaces;
said lenticule after removal from the donor cornea being treated according to a planned refraction correction to change an optical property of the lenticule such that, after insertion into a recipient cornea, the planned refraction correction in the recipient cornea results.

10. The method as claimed in claim 9 wherein the removal of the lenticule from the donor cornea does not change a refraction of the donor eye.

11. A computer program product having program code which, when executed on a computer, executes the method as claimed in claim 9.

12. A data medium having a computer program product as claimed in claim 11.

13. The method of claim 9, wherein said treatment comprises changing a physical, chemical or biological property of the lenticule.

14. The method of claim 13, wherein said treatment comprises changing a physical property of the lenticule resulting in a change to an optical power of the lenticule.

15. A method for eye surgery, wherein at least one cut surface is produced in the cornea by a treatment apparatus with a laser device, wherein the method is comprises the following steps:
providing corneal data that is based on data of a refraction correction,
determining the corneal cut surfaces, the corneal cut surfaces comprising at least a lenticular cut and a cap cut, on the basis of the corneal data,
producing a control data record for the corneal cut surfaces,
transmitting the control data to the treatment apparatus, and
producing the cut surfaces by actuating the laser device based on the control data record,
wherein the corneal cut surfaces are determined in such a way that a lenticule is isolated by the cut surfaces;
said lenticule after removal from the cornea being treated to change an optical property of the lenticule according to a planned refraction correction such that, after reinsertion into a recipient cornea, the planned refraction correction results.

16. The method as claimed in claim 15, wherein the removal of the lenticule does not cause a refractive correction in the donor cornea.

17. A computer program product having program code which, when executed on a computer, executes the method as claimed in claim 15.

18. A data medium having a computer program product as claimed in claim 17.

19. The method of claim 15, wherein said treatment comprises changing a physical, chemical or biological property of the lenticule.

20. The method of claim 19, wherein said treatment comprises changing a physical property of the lenticule resulting in a change to an optical power of the lenticule.

* * * * *

UNITED STATES PATENT AND TRADEMARK OFFICE
CERTIFICATE OF CORRECTION

| | | |
|---|---|---|
| PATENT NO. | : 11,241,336 B2 | Page 1 of 1 |
| APPLICATION NO. | : 16/300012 | |
| DATED | : February 8, 2022 | |
| INVENTOR(S) | : Mark Bischoff et al. | |

It is certified that error appears in the above-identified patent and that said Letters Patent is hereby corrected as shown below:

In the Specification

In Column 2, Line 9, delete "FLEx" and insert -- FLEX --, therefor.

In the Claims

In Column 12, Claim 10, Line 1, delete "9" and insert -- 9, --, therefor.

Signed and Sealed this
Twelfth Day of April, 2022

Drew Hirshfeld
*Performing the Functions and Duties of the*
*Under Secretary of Commerce for Intellectual Property and*
*Director of the United States Patent and Trademark Office*